United States Patent [19]

Barbarito et al.

[11] Patent Number: 4,827,919
[45] Date of Patent: May 9, 1989

[54] FEMORAL SPACER

[75] Inventors: James L. Barbarito, Ridgewood; William J. Cymbaluk, Jr., Edison; Matthew P. Poggie, Palisades Park, all of N.J.

[73] Assignee: Pfizer Hospital Products Group, Inc., New York, N.Y.

[21] Appl. No.: 923,256

[22] Filed: Oct. 27, 1986

[51] Int. Cl.⁴ .................................... A61M 37/00
[52] U.S. Cl. ............................... 128/92 Y; 623/22
[58] Field of Search ........... 128/92 Y, 92 YZ, 92 YK, 128/92 YW; 623/22, 23

[56] References Cited

U.S. PATENT DOCUMENTS

| | | | |
|---|---|---|---|
| 2,719,522 | 10/1955 | Hudack | 623/23 |
| 2,785,673 | 3/1957 | Anderson | 128/92 |
| 3,820,167 | 6/1974 | Sivash | 3/1 |
| 3,829,904 | 8/1974 | Ling et al. | 128/92 VP |
| 3,846,846 | 11/1974 | Fischer | 623/23 |
| 3,848,272 | 11/1974 | Noiles | 3/1 |
| 3,943,576 | 3/1976 | Sivash | 3/1 |
| 3,996,625 | 12/1976 | Noiles | 3/1.912 |
| 4,012,796 | 3/1977 | Weisman et al. | 3/1.91 |
| 4,064,567 | 12/1977 | Burstein et al. | 623/23 |
| 4,077,070 | 3/1978 | Sivash | 623/22 |
| 4,080,666 | 3/1978 | Fixel | 3/1.91 |
| 4,187,559 | 2/1980 | Grell et al. | 3/1.91 |
| 4,231,120 | 11/1980 | Day | 3/1.91 |
| 4,292,694 | 10/1981 | Koeneman | 3/1.91 |
| 4,292,695 | 10/1981 | Koeneman | 3/1.91 |
| 4,302,855 | 12/1981 | Swanson | 623/23 |
| 4,357,716 | 11/1982 | Brown | 623/23 |
| 4,404,692 | 9/1983 | Eftekhan | 128/92 VP |
| 4,459,708 | 7/1984 | Buttazzoni | 3/1.91 |
| 4,661,112 | 4/1987 | Müller | 623/22 |
| 4,770,660 | 9/1988 | Averill | 623/23 |

FOREIGN PATENT DOCUMENTS

83/02555 8/1983 PCT Int'l Appl. .
8801854 3/1988 PCT Int'l Appl. .

Primary Examiner—C. Fred Rosenbaum
Assistant Examiner—Mark F. Colosimo
Attorney, Agent, or Firm—Peter C. Richardson; Lawrence C. Akers; Elizabeth O. Slade

[57] ABSTRACT

A femoral spacer for positioning a femoral prosthesis is disclosed comprising a hollow body portion having an outside surface and an inside surface. The outside surface is adapted to contact the intramedullary canal wall, and the inside surface is adapted to contact the proximal portion of the prosthesis such that the prosthesis is substantially centered within the intramedullary canal.

10 Claims, 2 Drawing Sheets

U.S. Patent May 9, 1989 Sheet 1 of 2 4,827,919
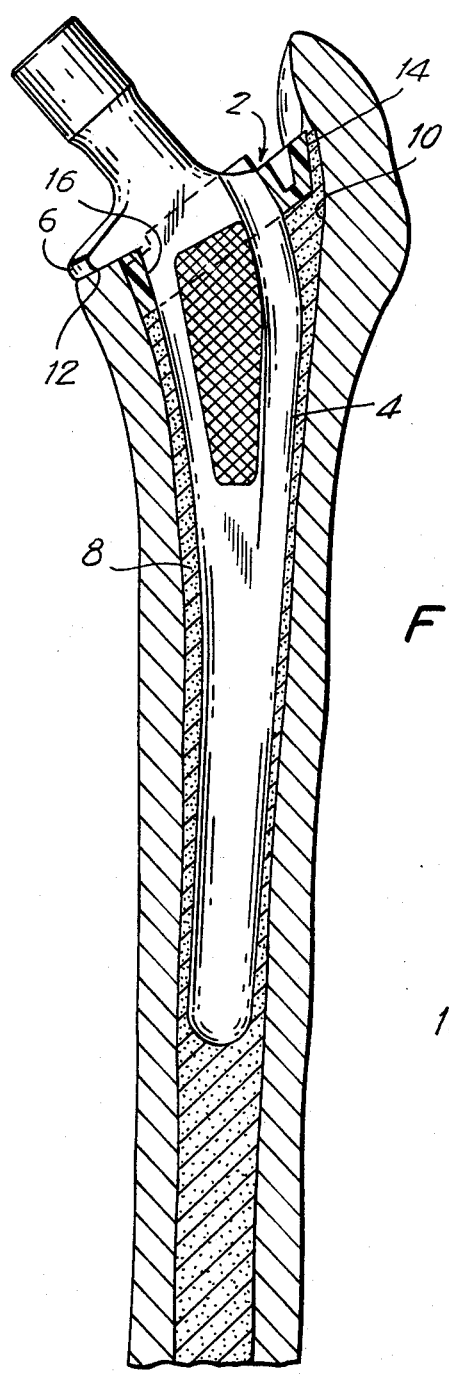
FIG. 3
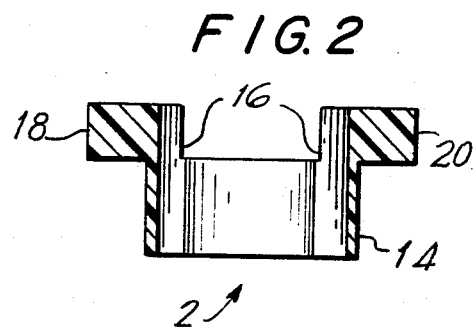
FIG. 1
FIG. 2

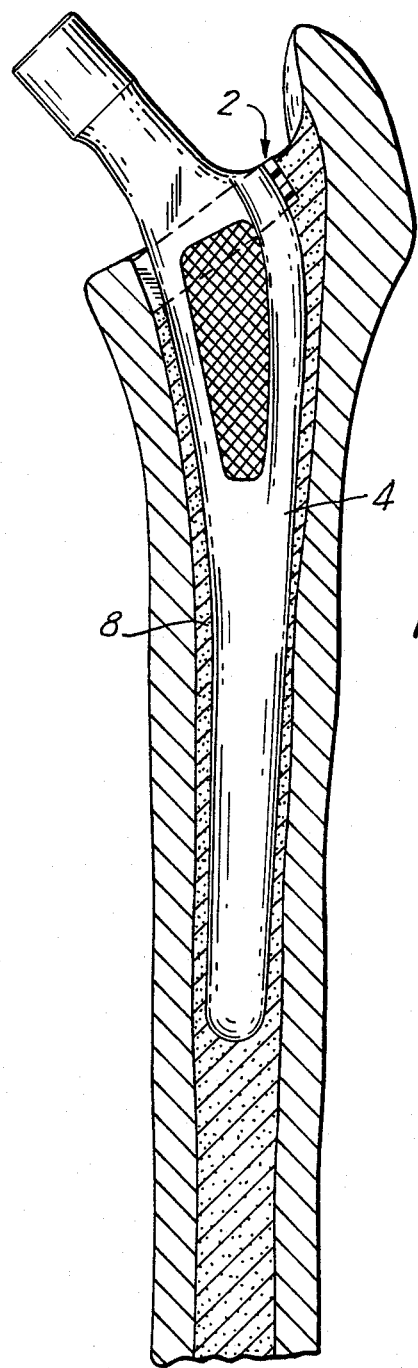
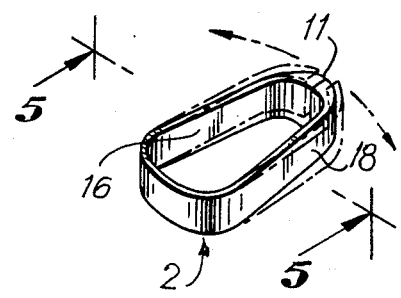
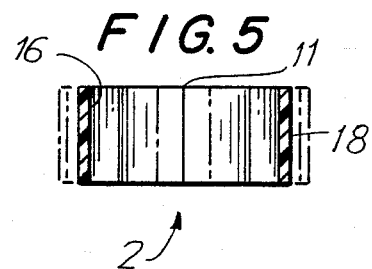

FEMORAL SPACER

BACKGROUND OF THE INVENTION

The present invention relates to a femoral spacer for positioning a femoral prosthesis within the intramedullary canal of a bone, and the method of use of the spacer. More particularly, the invention relates to a device wherein the proximal portion of the femoral prosthesis is substantially centered within the intramedullary canal.

Current methods which are used to center the proximal portion of a femoral prosthesis include substantial surgical skill and judgment. However, the major difficulty in relying on surgical judgment is its inexact nature, leading to inconsistent results over a number of such operations. There is a need to locate the prosthesis positively and consistently in a substantially centered position within the canal, because location of the prosthesis in the intramedullary canal is critical to the longevity of hip replacement. If the prosthesis is not positioned in a substantially centered position, the prosthesis can cause abnormal and detrimental stress to the cement mantle thereby leading to failure of the prosthesis and the need for a revision of the prosthetic hip.

SUMMARY OF THE INVENTION

The main object of the present invention is to provide a simple economical device for advantageously positioning a femoral prosthesis in an intramedullary canal. This object and others are achieved by the novel device of the present invention which substantially centers the proximal portion of a femoral prosthesis within the intramedullary canal. The device is comprised of a hollow body portion having an outside surface and an inside surface, a substantial portion of the outside surface adapted to contact the intramedullary canal wall and a substantial portion of the inside surface adapted to contact a proximal portion of the prosthesis, whereby the proximal portion of the prosthesis is substantially centered within the intramedullary canal.

The device may be made of, for example, polymethyl methacrylate, and is preferably made of a radiopaque material. In a preferred embodiment of the device, the outside surface of the body portion includes anterior and posterior shoulders, with the shoulders having undersides that are adapted to rest on the femur.

The present invention also embraces a femoral spacer for positioning a femoral prosthesis having a medial collar. In this embodiment the proximal portion of the prosthesis is substantially centered within the intramedullary canal with the medial collar of the prosthesis resting directly on the calcar portion of the resectioned femur.

The present invention further includes a method for positioning the proximal shoulder area of a femoral prosthesis in a femoral canal comprising the steps of: (a) reaming the femoral canal, (b) filling the canal with bone cement, (c) placing the device into the bone cement so that the outside contacts the intramedullary canal wall, and (d) inserting the femoral prosthesis into the filled canal through the device.

BRIEF DESCRIPTION OF THE DRAWINGS

Novel features and advantages of the present invention, in addition to those mentioned above, will become apparent from a reading of the following detailed description in conjunction with the accompanying drawings wherein:

FIG. 1 is a side view in elevation of the femoral spacer.

FIG. 2 is a cross-sectional view along the line 2—2 of FIG. 1.

FIG. 3 is a semi-schematic view of the femoral spacer of the present invention in place, wherein the spacer is positioned such that the femoral prosthesis is substantially centered within the intramedullary canal and the shoulders are resting on the calcar portion of the bone.

FIG. 4 is a side view in elevation of the femoral spacer without shoulders.

FIG. 5 is a cross-sectional view of FIG. 4 taken along lines 5—5.

FIG.6 is a semi-schematic view of the femoral spacer without shoulders wherein the spacer is positioned such that the femoral prosthesis is substantially centered within the intramedullary canal.

DESCRIPTION OF THE PREFERRED EMBODIMENT

In FIGS. 1-6 is illustrated a femoral spacer 2 for positioning of a femoral prosthesis 4 within an intramedullary canal in the body of a patient. The femoral spacer 2 comprises a hollow body portion 24 having an outside surface 14 and an inside surface 16.

As can be seen in FIG. 3, a substantial portion of the outside surface 14 contacts the intramedullary canal wall 10. A substantial portion of the inside surface 16 of the spacer 2 contacts the femoral prosthesis 4.

Preferably, spacer 2 fits snugly within the intramedullary canal wall 10, and most preferably the outside surface 14 is congruent with the canal 10, while the inside surface 16 is congruent with the femoral prosthesis 4. Most preferably, the spacer 10 includes anterior shoulder 18 and posterior shoulder 20, with each of the shoulders having undersides that are adapted to rest on the femur.

The body portion of the spacer 2 tapers generally from an outside surface width of from about 25 mm. to 30 mm. to an inside surface width of from about 15 mm. to 25 mm. The length of the inside surface 16 of the spacer 2 is from about 20 mm. to 35 mm. and is 7 mm. to 15 mm. high. The outside surface is 30 mm. to 50 mm. in length. The body portion is preferably made of polymethyl methacrylate or methylmethacrylate, most preferably made radiopaque by the addition of radiopaque material, for example, barium sulfate. Other suitable materials inclue a biocompatible metal, for example, cobalt chrome alloy or titanium alloy, and a polymer such as an ultra high molecular weight polyethylene. The spacer is preferably produced by injection molding.

In FIG. 1 is shown a femoral spacer 2 for a femoral prosthesis 4 having a medial collar 6. In this embodiment the proximal collar portion of the femoral prosthesis 4 rests directly on the calcar portion 12 of the resectioned femur. In this way, in addition to centering the femoral prosthesis 4 within the intramedullary canal 8, the spacer contains the cement within the bone thereby pressurizing the cement within the canal.

In FIG. 4 a further embodiment of the invention is shown without shoulders particularly adapted to center a collared or non-collared prosthesis 13 within the intramedullary canal. The device can also be supplied with an opening, as shown at 11, to better enable the surgeon to place it in an irregular shaped canal. In this embodiment the spacer can be positioned at the top cut end of the bone or at some other point in the proximal femur with the location being determined by the canal geometry.

In use, the femoral canal is reamed out by means of rasps to provide sufficient room for the femoral prosthesis and the bone cement. The canal is then filled with bone cement. In the next step the surgeon can either place the spacer on the femoral prosthesis and insert the two as a unit, or can insert first the spacer and then insert the prosthesis through the spacer and into the filled canal. The spacer can also be attached to the prosthesis during the manufacturing process thereby eliminating the two step process. Additionally, the spacer can be located further down the canal rather than resting on the calcar portion of the resected femur.

The femoral spacer of the present invention eliminates many of the problems of previously used surgical methods of positioning femoral prosthesis. Further, the spacer provides a reliable and relatively simple system whereby surgeons can depend on proper positioning of a prosthesis, thereby reducing the risk of prosthesis failure. The novel device of this invention has the further advantage of being effective and economical. In addition, it is of relatively uncomplicated design, offers easy manipulation and insertion, and is adaptable for use with various surgical techniques.

This invention can be used to locate any prosthesis that relies on cemented, or the like, medullary fixation. A spacer for other joints would be used in a similar fashion. In any case, the device must be in sufficient contact with both the intramedullary stem and the intramedullary canal, to insure the appropriate position. Possible applications include the humeral component of a shoulder joint and the humeral and ulnar components of an elbow joint.

Further modifications will occur to those skilled in the art. The scope of the invention is defined by the appended claims and should not be understood as limited by specific embodiments described herein.

What is claimed is:

1. A proximal femoral spacer for positioning a femoral prosthesis having a medial collar within the intramedullary canal of a resectioned femur, said spacer comprising a body portion having an outside surface and an inside surface, wherein a substantial portion of the outside surface in use contacts the intramedullary canal wall and a substantial portion of the inside surface contacts a proximal portion of the prosthesis, whereby the proximal portion of the prosthesis is substantially centered within the intramedullary canal but with the medial collar of the prosthesis resting directly on the calcar portion of the resectioned femur, wherein the outside surface of the body portion includes anterior and posterior shoulders, said shoulders having undersides that rest on the femur.

2. A spacer according to claim 1 wherein the spacer comprises at least one material selected from the group consisting of polymethyl methacrylate and methylmethacrylate.

3. A spacer according to claim 1 wherein the outside surface is substantially congruent with the femoral canal, and the inside surface is substantially congruent with the femoral prosthesis.

4. A spacer according to claim 2 wherein the body portion comprises a radiopaque material.

5. A method of positioning the proximal shoulder area of a femoral stem prosthesis in a femoral canal comprising the steps of:
   (1) providing a device of claim 1,
   (2) reaming the femoral canal,
   (3) filling the femoral canal with bone cement,
   (4) placing the device into the bone cement so that the outside contacts the intramedullary canal wall, and
   (5) inserting the femoral stem prosthesis into the filled canal through the device.

6. A spacer according to claim 1, wherein said body portion is substantially annular-shaped.

7. A spacer according to claim 1, wherein said outer surface and said inner surface of said spacer are substantially smooth and unperforated.

8. A spacer according to claim 4, wherein said radiopaque material comprises barium sulfate.

9. A spacer according to claim 1, wherein said body portion has a slit located therein which enables said spacer to be placed into an irregular-shaped intramedullary canal.

10. A spacer according to claim 6, wherein said body portion includes also a bore located between said inside surface and said outside surface, said bore enabling excess bone cement to be to added to or removed from the intramedullary canal during the procedure of filling the femoral canal with bone cement.

* * * * *